United States Patent [19]
McClellan

[11] Patent Number: 6,007,576
[45] Date of Patent: Dec. 28, 1999

[54] END TO SIDE ANASTOMIC IMPLANT

[76] Inventor: Scott B. McClellan, 1350 N. 1390 E., Heber City, Utah 84032

[21] Appl. No.: 09/020,097
[22] Filed: Feb. 6, 1998
[51] Int. Cl.⁶ ....................................................... A61F 2/06
[52] U.S. Cl. ................................... 623/1; 623/12; 623/11
[58] Field of Search ..................................... 623/1, 11, 12

[56] References Cited

U.S. PATENT DOCUMENTS

| | | |
|---|---|---|
| 2,127,903 | 8/1938 | Bowen . |
| 3,683,926 | 8/1972 | Suzuki . |
| 4,294,255 | 10/1981 | Geroc . |
| 4,366,819 | 1/1983 | Kaster ..................................... 128/334 |
| 4,601,718 | 7/1986 | Possis et al. . |
| 4,721,109 | 1/1988 | Healey . |
| 5,156,619 | 10/1992 | Ehrenfeld . |
| 5,425,739 | 6/1995 | Jessen ..................................... 606/155 |
| 5,443,497 | 8/1995 | Venbrux . |
| 5,456,712 | 10/1995 | Maginot . |
| 5,456,714 | 10/1995 | Owen ......................................... 623/1 |
| 5,480,434 | 1/1996 | Eckstein et al. . |
| 5,591,206 | 1/1997 | Moufarrège . |
| 5,643,340 | 7/1997 | Nunokawa ................................. 623/1 |

Primary Examiner—David H. Willse
Assistant Examiner—Suzette J. Jackson
Attorney, Agent, or Firm—Trask, Britt & Rossa

[57] ABSTRACT

An anastomosis apparatus includes a first rigid element and a second rigid element. The first element defines a first passageway or lumen which extends along its entire length. In construction the first element includes a first tubular portion in association with a first flange disposed on one end of the first tubular portion. The first flange is fixedly secured to the first tubular portion. The second element defines a second passageway along its entire length which is dimensioned to slidably receive and retain the first tubular portion. The second element includes a second tubular portion in association with a second flange disposed on a proximal end of the second tubular portion. An engagement of the first element with the second element about an opening defined in the blood vessel of a patient results in a fixed spatial relationship of the first element relative to the second element whereby the first passageway is retained in a generally fixed spatial relationship with the lumen of the aforesaid blood vessel.

24 Claims, 5 Drawing Sheets

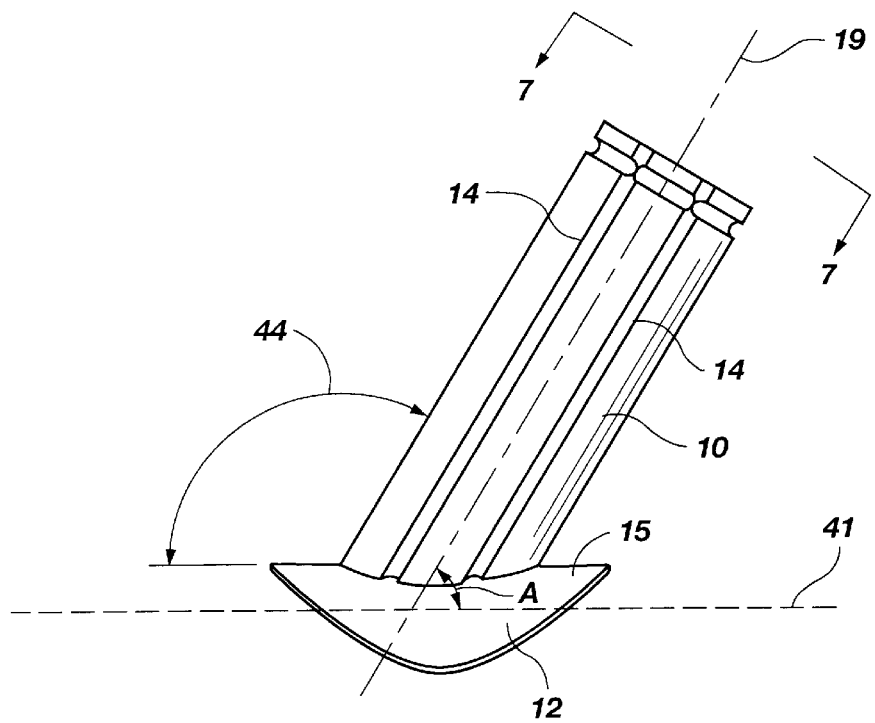
Fig. 6
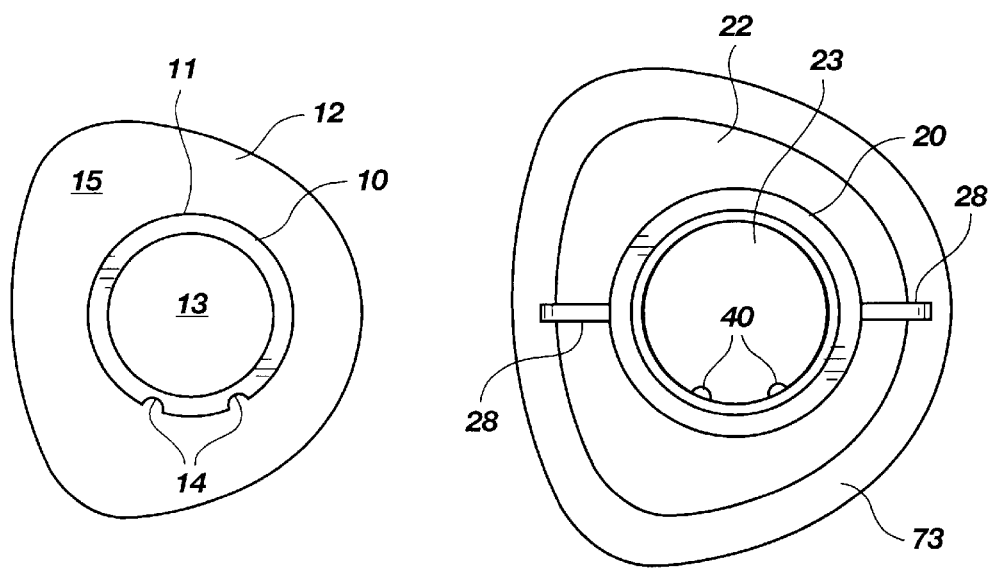
Fig. 7
Fig. 8

END TO SIDE ANASTOMIC IMPLANT

BACKGROUND OF THE INVENTION

1. Field of the Invention

This invention relates to anastomotic implants. More particularly, the invention is directed for use in effecting an end to side anastomotic juncture.

2. State of the Art

An objective of vascular reconstructive surgery is the reconstitution of blood flow from a blood vessel which has ceased effective operation. The necessity of grafting a replacement vessel to the sidewall of the damaged blood vessel arises with significant frequency. Cardiovascular disease is the current paramount cause of natural deaths in the U.S. Approximately 485,000 coronary bypass procedures requiring vascular anastomosis performed annually plus one million other vascular surgeries requiring vascular anastomosis (ex. shuts, fistular, fem-fem bypass) are performed annually in the U.S. Of the aforesaid 485,000 bypass procedures each bypass procedure requires on average between 2–5 anastomosis procedures to be effected. It follows effectively that end-to-side anastomosis techniques and implants are of critical importance in the medical community. As used herein, "end-to-side" is independent of blood flow direction and, therefore, "end-to-side anastomsis" includes an end-to-side anastomsis as well as a side-to-end anastomosis. Vascular grafts may be formed from autogenous blood vessels harvested from other locations in the patient's body or alternatively may be manufactured from synthetic or non autogenous vessels.

Coronary bypass surgery is the commonly-adopted treatment for coronary ischemic (heart attacks). This surgery is time consuming and requires an inventory of skilled techniques. The general procedure may require between four to six hours and is typically accompanied by the surgeon's stopping the patient's heart in order to facilitate delicate suturing of vascular tissue. The success of such procedures is heavily dependent on the individual skills of the participating surgeons. Vascular anastomosis forms an essential component in a typical coronary bypass procedure.

An anastomosis typically includes a manually sutured junction of the graft vessel with the effected vascular vessel. Understandably, as the size, e.g. diameter, of the involved vessels decrease in size the ability of the surgeon to effect a suture having long-term viability is severely challenged.

The time consumed in suturing the vessels in a bypass procedure can easily exceed fifty percent (50%) of the time involved in the procedure. It follows that any procedure or apparatus which would decrease the time commitment necessitated by suturing holds potential in this environment. Furthermore, significant reduction in the time involved in effecting the anastomosis itself could potentially lead to the elimination of the need for cardiopulmonary bypass, which, in and of itself, would be a considerable step forward in lessening the risk associated with this type of procedure.

Of considerable concern in bypass procedures is the potentiality of vascular graft failure. A principal cause of such failure is turbulent blood flow over a rough suture line. Other concerns include the quality of the involved graft vessel, a potential mismatch in the diameter of the treated vessel and the graft, and an improper angle of bifurcation at the anastomosis juncture.

SUMMARY OF THE INVENTION

An end-to-side vascular anastomosis apparatus is disclosed. The apparatus includes a first element and a second element. The first element defines a first passageway or lumen which communicates with a portion of the first element which is configured for insertion within the lumen of a patient's first blood vessel. The first passageway further communicates with structure adapted for connection to a graft or a second blood vessel whereby upon an insertion of said first portion into the lumen of a patient's blood vessel, the first passageway functions to relay blood from within the lumen of the blood vessel outwardly through the sidewall of the blood vessel to the graft or second blood vessel. An engagement of the first element with the second element produces a rigid apparatus structure whereby the orientation of the first passageway relative to the first blood vessel is generally spatially fixed.

The following description of the invention refers to the implantation of the invention within the sidewall of a patient's blood vessel. It should be understood that the application may also have application to other parts of the body as well, e.g. to body organs.

The first element includes a first tubular portion and a first flange disposed on an end thereof. The first tubular portion defines a first passageway or lumen which extends through the entire length of the first element. The first element is formed of a rigid material or combination of materials. The flange of the first element is configured to be inserted through a hole or vascular foramen (e.g., a circular aperture having a preselected diameter to match the outer diameter of the tubular portion of the first element)in a blood vessel and thereafter be positioned against the surface of an inner sidewall of the blood vessel. In preferred constructions the surface of the flange which is intended to be positioned contiguous with the inner vascular sidewall is configured to have a convex surface generally corresponding to the surface of the inner vascular sidewall.

The second element includes a second tubular portion and a second flange disposed on one end of the second tubular portion. The second tubular portion of the second element defines a passageway or lumen which is dimensioned to slidably receive and retain a portion of the first tubular portion of the first element. In practice, once the flange of the first element is inserted into the aperture within the sidewall of the blood vessel, a portion of the first tubular portion of the first element extends outwardly from the blood vessel. The second element is thereafter aligned with the first element and the first tubular portion of the first element is inserted into the passageway or lumen of the second element.

A retaining means, which may be associated with either the first element or the second element or in some configurations with both of the elements, may thereafter be used to retain the two elements in a fixed relationship or union relative to each other. In some constructions, this union of the two elements may be a detachable union.

The second flange of the second element includes a surface which is configured to be abutted against the external sidewall of the aforesaid blood vessel opposite from the first flange of the first element. Stated otherwise, the first flange has a surface which is configured to have a concave surface which corresponds to the surface of the exterior vascular sidewall.

The second element is preferably fabricated from a material which is either rigid or semi-rigid, whereby upon an engagement of the first element and the second element, a construction is formed which is generally rigid and which is fixedly positioned about the vascular sidewall to establish a first passageway or lumen of fixed orientation relative to the lumen of the blood vessel.

The first element may also include a means of registering the second element in alignment with the second element and retaining that alignment while the union of the two elements is effected. This registration means may also function to retain the two elements in alignment with one another while the two elements are united together.

The distal end of the second tubular portion may be fitted with structure adapted for connection with either a graft or with a second blood vessel. The apparatus thereby provides a construction for transmitting blood from the first blood vessel to a second blood vessel. It should be appreciated that in some instances, the first blood vessel and the second blood vessel may be the same vessel.

The second element may also include a securement means for securing the second element to tissue surrounding the anastomotic apparatus.

BRIEF DESCRIPTION OF THE DRAWINGS

FIG. 6 is a side view of the first element of the apparatus;

FIG. 7 is a top view of the first element of the apparatus;

FIG. 8 is a top view of the second element of the apparatus;

DETAILED DESCRIPTION OF THE ILLUSTRATED EMBODIMENT

Figure 1:
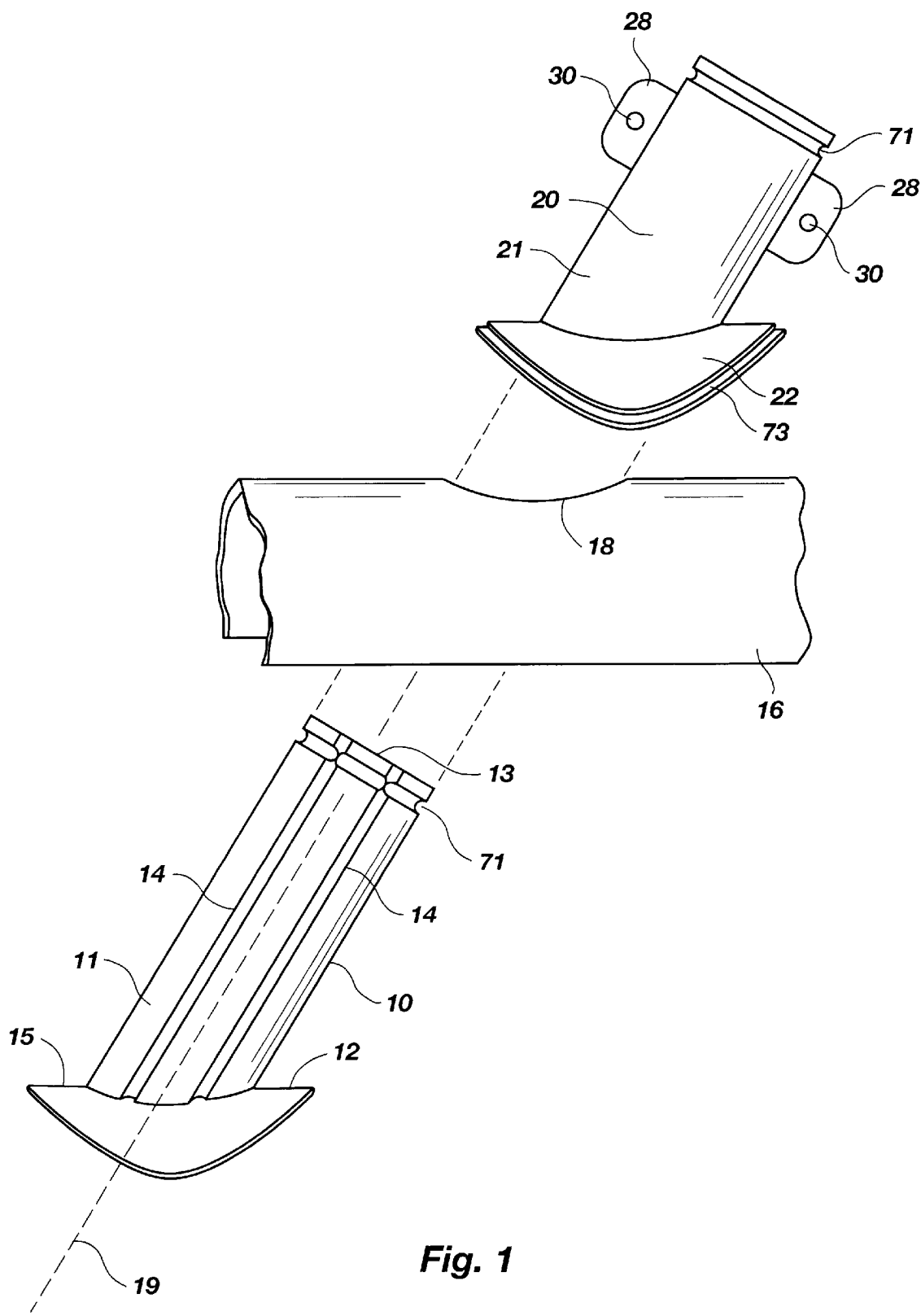
FIG. 1 is a side view of the anastomotic apparatus of the instant invention shown in an exploded view.

As shown in FIG. 1 an anastomotic apparatus of the invention includes a first element 10 and a second element 20. The two elements are designed to engage with one another about an aperture or opening in the side wall of a blood vessel 16 to provide a fluid passageway from the lumen of the blood vessel 16 to a second blood vessel or organ.

The first element 10 includes a first tubular portion 11 and a first flange 12, which is connected to the tubular portion 11 at a first end of the tubular portion 11. In preferred constructions, the first tubular portion 11 and the first flange 12 are manufactured as an integral structure. As shown in FIGS. 1 and 7, the first tubular portion 11 is a generally elongate right cylindrical tube which defines a first passageway or lumen 13 which extends through the entire length of the first tubular portion. The lumen 13 is generally right cylindrical in shape. The first tubular portion 11 and the lumen 13 are concentrically positioned about a longitudinal axis 19.

The lumen 13 includes a diameter which remains constant over the length of the lumen. Equally, the first tubular portion 11 also defines a diameter which remains constant over the length of the tubular portion.

The sidewall of the first tubular portion 11 is shown as defining two linear channels 14 within the external sidewall of the tubular portion. While the drawings indicate the presence of two such channels 14 it should be understood that any number of such channels could be utilized in the invention, including a single channel. As shown in FIG. 1 each of these channels 14 is generally linear in configuration and semicircular in cross section. Each of these channels 14 forms a part of a means for registering and aligning the first element 10 with the second element 20 for purposes of assisting the user in assembling the two elements into an operative apparatus.

Figure 2:
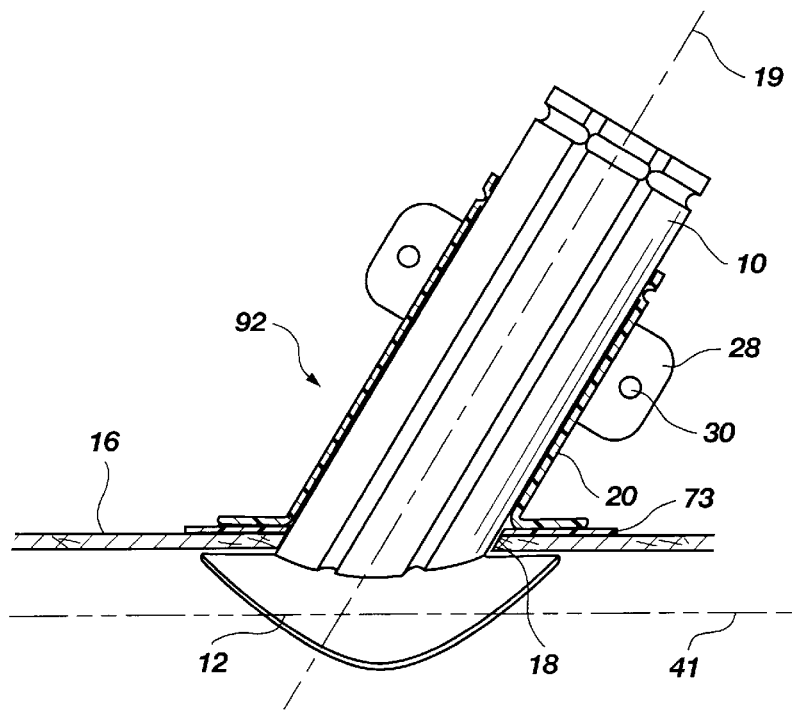
FIG. 2 is a cross sectional side view of the apparatus of FIG. 1.
Figure 3:
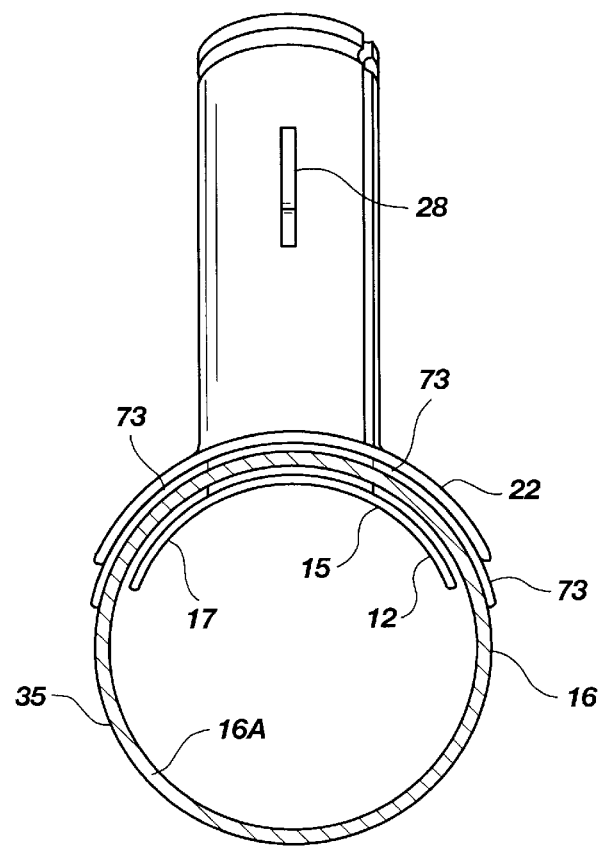
FIG. 3 is an sectional view of the apparatus of FIG. 2 taken along section lines 3—3.

The first flange 12 is shown connected to the first end of the first tubular portion 11. The flange 12 defines a convex upper surface 15 and a concave lower surface 17 as shown in FIG. 3. The first flange 12 defines a longitudinal axis 41 as shown in FIG. 2. The first tubular member 11 and the first flange 12 are secured to one another and are manufactured of materials of sufficient rigidity that the orientation of the longitudinal axis 19 is spatially fixed relative to the longitudinal axis 41. It follows that the first flange 12 is not permitted to move relative to the first tubular portion 11. In some preferred constructions the longitudinal axes actually intersect as shown in FIG. 6 at an angle "A." This angle "A" may have a degree measure between zero degrees and one hundred and eighty degrees. In preferred constructions the angle "A" is within the range of thirty and 150 degrees.

The upper surface 15 may be configured to correspond with the shape and configuration of the surface of the inner sidewall 16A of the blood vessel 16 in which the first flange 12 is to be positioned. Stated otherwise, the curvature of the upper surface 15 of the flange 12 is configured to correspond to the curvature of the surface of the inner sidewall of the blood vessel 16 as shown in FIG. 3.

In a preferred construction the first flange 12 is constructed such that upon the engagement of the first and second elements, the first flange 12 abuts against the surface of the inner sidewall over substantially the entire surface of the upper surface 15 of the flange 12. It follows that the abutting surfaces of the internal sidewall of the blood vessel 16 and the first flange surface 15 will have generally identical radii of curvature.

The first element 10 is fabricated to be generally rigid. In preferred constructions the first element 10 may be constructed of materials which exhibit higher moduli of elasticity and rigidity with minimal or no creep. Some materials which are contemplated for use in manufacturing the first element are titanium, stainless steel, graphite, and some non-deformable plastics such as ultrahigh density polyethylene (UHDPE), polycarbonate and acrylonitrile-butadiene-styrene copolymer (ABS). Some ceramic materials may also be used. Depending on the target vessels, the pulsatile flow conditions and the level of activity, the local geometry surrounding the anastomosis site can change thereby altering the flow characteristics at or near the bifurcation. Changes in local geometry can have very deleterious effects on the patency of the inlet anastomosis as well as the distal graft and distal anastomosis. A rigid apparatus of the instant invention is directed to preserve the inlet and outlet geometries thereby increasing the level of performance and patency of the anastomosis and the graft.

Preferably, the first element 10 is fabricated from materials which may be coated with substances which limit or preclude the likelihood of rejection of the implant by the patient. In preferred embodiments of the invention the first element 10 is manufactured from a material which provides a surface which is inelastic, firm, rigid, and non-bendable thereby rendering the first element suitable for being coated with a nonthrombogenic material such as with a pyrolytic carbon coating. Pyrolytic carbon is considered as a material which is one of the most biocompatible and further a material which has one of the smallest likelihoods of initiating a thrombogenic reaction. The choice of a material which is susceptible to a coating with pyrolytic carbon is therefore seen as a means of providing a structure which is both sufficiently rigid to maintain and/or preserve the local geometry under varying pressure and flow conditions, thereby preserving the desired flow characteristics and furthermore is adapted for minimizing any chance of rejection by the patient's immune system.

The second element 20 includes a second tubular portion 21 and a second flange 22 which is secured to one end of the second tubular portion 21 as shown in FIG. 1. In preferred constructions, the second tubular portion 21 and the second flange 22 are manufactured as an integral structure.

In contrast to the first element, the second element may be manufactured from most hard, non-restorable plastics. Since the second element will not be direct contact with the patient's blood stream, the concern for biocompatibility is of less importance.

Figure 5:
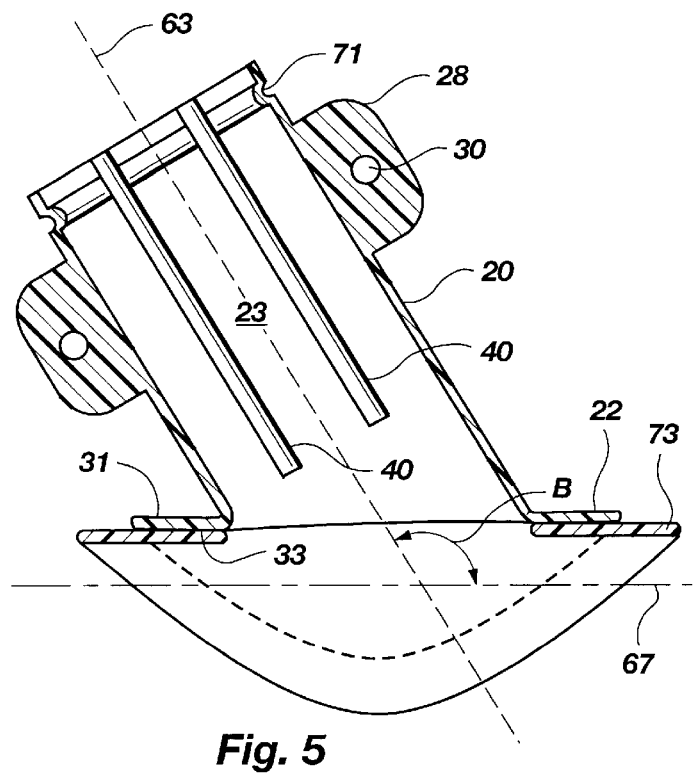
FIG. 5 is a cross sectional view of the second element of the apparatus.

As shown in FIG. 5 and 8, the second tubular portion 21 of second element 20 defines a second passageway or lumen 23 which extends through the length of the second tubular portion 21. The lumen 23 is generally right cylindrical in shape and is concentrically disposed about a longitudinal axis 63. The sidewall of the second tubular portion 21 defines a diameter which remains generally constant over its length and it too is oriented concentrically with respect to axis 63. The second lumen 23 is dimensioned to receive and retain the first tubular portion 11 of the first element 10. It follows that the diameter of the lumen 23 is slightly larger dimensionally than the diameter of the first tubular portion 11.

The inner sidewall of the tubular portion 23 defines two elongate, linearly configured extensions or splines 40 as shown to advantage in FIG. 5. Each of these splines is dimensioned and otherwise configured to be slidably received within a respective channel 14 defined within the external sidewall of the tubular portion 11 of the first element 10. The engagement of a spline 40 with its respective channel 14 forms a means of aligning the first element with the second element during the assembly of the anastomotic apparatus. As the first tubular portion 11 of the first element 10 is inserted into the lumen 23 of the second element 20, the user aligns the splines 40 with the channels 14. Once aligned, the splines 40 guide the passage of the first tubular portion 11 through the lumen 23 and thereby preclude a rotation of the tubular portion 11 within the lumen 23. As stated with respect to the channels 14, the number of splines may vary. Although two splines 40 are illustrated, it should be understood that any number of splines may be defined on the inner sidewall of the second tubular portion, including a single spline 40.

The second flange 22 of the second element 20 includes an upper surface 31 and a lower surface 33. The surfaces 31 and 33 are disposed about a longitudinal axis 67. The second flange 22 and the second tubular portion 21 are fabricated of rigid materials such that the respective longitudinal axes 67 and 63 of these members are retained in a fixed spatial relationship to one another. In preferred embodiments the two axes 67 and 63 actually intersect one another as shown in FIG. 5 at an angle "B". Angle "B" may vary between zero degrees and 180 degrees. Preferably, angle "B" varies within the range of thirty degrees and 150 degrees.

The anastomosis of the invention may be optimized for a specific range of variability in blood flow rates, blood vessel diameters, graft lengths, bifurcation ratios and pulsatile flow characteristics. Thereby the bifurcation angle 44 as shown in FIG. 6 may be varied due to optimization constraints. The bifurcation ratio is the diameter of the bypass graft to the diameter of the primary vessel. As the ratio approaches 1 the vessel diameter equals the primary vessel diameter. The amount or extent of intraluminal surface area contacted by the first element and extravascular surface area contacted by the second element is related to the bifurcation ratio.

Figure 4:
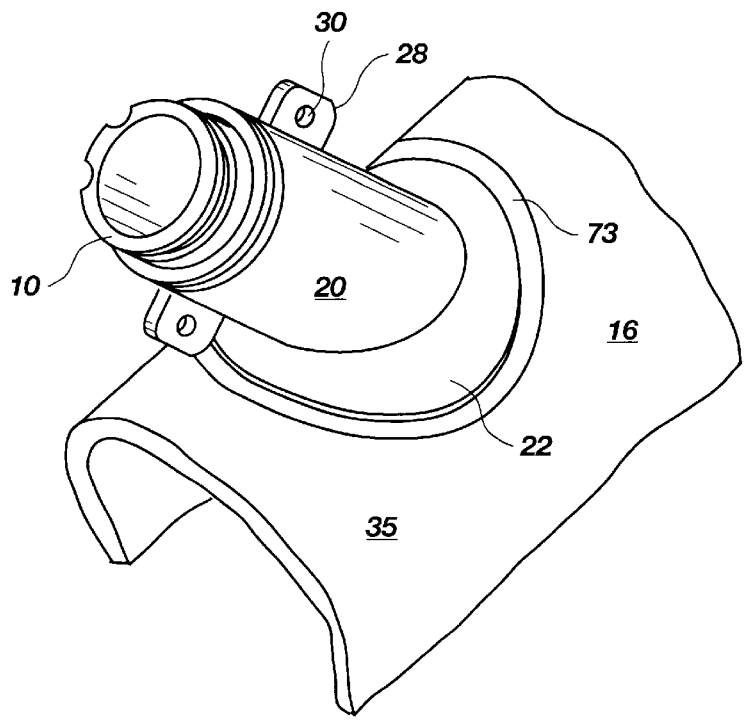
FIG. 4 is a perspective view of the apparatus of FIG. 2.

The lower surface 33 of the second flange 22 defines a concave surface. In preferred configurations, the lower surface 33 is configured to generally correspond to the exterior sidewall surface 35 of the blood vessel 16 proximate the opening or vascular foramen 18. The lower surface 33 is constructed to abut against the exterior sidewall surface 35 and define a form fitting abutment against that surface 35. In preferred constructions, the lower surface 33 is configured such that it abuts the exterior sidewall surface 35 over its entire surface. In these constructions, the curvature of the lower surface 33 generally corresponds to the curvature of the surface 35 of the blood vessel 16. The second element 20 may also include one or more extensions 28 which extend outwardly from the exterior sidewall of the second tubular portion 21. Each of these extensions 28 may define an aperture 30 therethrough which provides the user with a means of securing the apparatus to surrounding tissue and/or fascia by passing suturing thread through the aperture and thereafter through the surrounding tissue thereby interconnecting the apparatus 9 to the surrounding tissue. As shown in FIG. 4, these extensions may be positioned diametrically opposite one another about the second element 20. The extensions 28 demonstrated may alternatively be immobilized polymeric fastening strips for stress relief. They can be rigid or pliable, sutured or stapled to the surrounding facia expressly for immobilizing the implant and decreasing stress concentrations at the anastomosis site.

Figure 9:
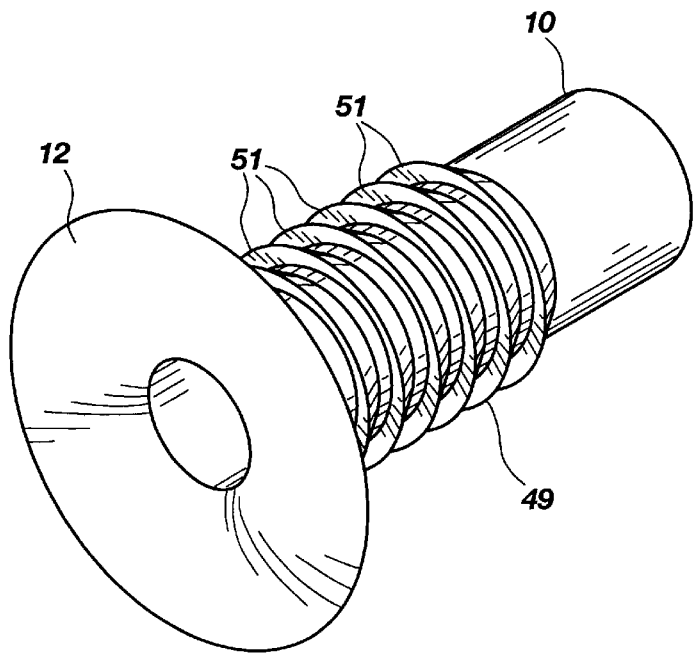
FIG. 9 is a perspective view of a first element of the apparatus shown fitted with a means of securing the first element to the second element.
Figure 10:
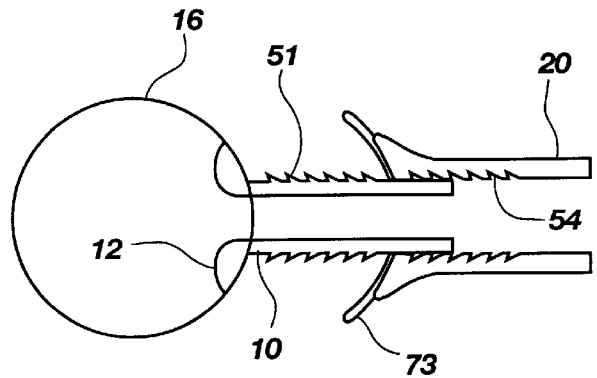
FIG. 10 is a side view of the apparatus illustrating a means of interconnecting the two elements of the apparatus.
Figure 11:
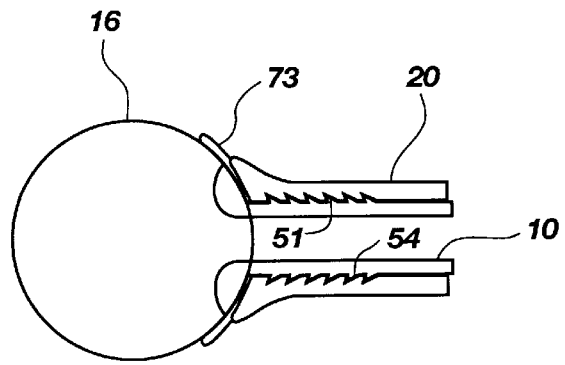
FIG. 11 is a side view of the apparatus illustrating the means of FIG. 10 in a closed condition.

FIG. 9 illustrates a first element 10 fitted with a means 49 of interconnecting the first element 10 with a second element 20. The first element 10 is shown as having a plurality of ring-like members 51 which encircle the tubular portion 11 of the element 10. The association of members 51 defines a series of racheting teeth which are dimensioned to interact with a series of correspondingly dimensioned recesses or openings 54 in the interior sidewall surface of the second element 20. As the first element is inserted into the passageway defined within the second element 20, the various ring-like members 51 are received within respective openings 54 defined within the second element thereby forming a union of the first and second elements. Alternative means of securing the two elements together may include a band-like structure which is positioned about the circumference of the second element and is constricted about that element to form a pressure union of the second element with the first element.

In operation, the user first makes an opening 18 in the subject blood vessel 16. In contrast to previous anastomotic operations which involve the making of an incision in the blood vessel, the instant invention requires the user to actually cut an opening having a diameter of preselected dimension, e.g., a circular or elliptical opening. The first flange 12 is inserted through the opening 18 and is thereafter positioned such that the upper surface 15 is abutted against the inner sidewall of the vessel 16. The first tubular portion 11 of the first element 10 is then inserted through the lumen 23 of the second element 20 such that the concave surface 33 is brought into abutment against the external sidewall surface of the vessel 16. By urging the second element 20 along the length of the first element 10 and by using the racheting securement means disclosed above, the user may tighten the first and second element's engagement against the blood vessel sidewall sufficiently to ensure a secure engagement while yet avoiding damaging the vessel sidewall.

In preferred constructions, the rigidity of the construction of the two elements 10 and 20 and the nature of their engagement define a structure wherein the two elements are retained fixedly together. This in turn provides the user with a fixed egress angle for the flow of blood out of the blood vessel 16. Due to the rigidity of the construction of the two elements and their engagement the longitudinal axis 19 is retained in a fixed spatial orientation relative to the longitudinal axes 63 and 67. In the most preferred constructions, all of the longitudinal axes 19, 41, 63 and 67 are held in fixed orientations relative to one another upon the engagement of the two elements 10 and 20.

In order to facilitate the interconnection of a graft to the first element 10, that element may include a circular channel 71 which is defined proximate the free end of that element. Various means known in the art, e.g. a constrictive band, may be utilized in conjunction with the channel 71 as a means of retaining the graft (not shown) to the element 10.

In a preferred construction, a washer 73, which may be partially degradable may be fixed and/or immobilized to the flange of the second element 20. In alternative embodiments the washer 73 may be simply positioned on the vessel and retained in place by the pressure of the second element, i.e. the washer is not fixed or secured to the second element in this alternative embodiment.

It is recognized that with the anastomosis in place there are two potential passages for blood flow through the anastomosis. The first passage is through the passageway of the first element and thereafter into the vascular graft secured to the end of the first element. The second passage is behind the first element, through the induced vascular foramen and thereafter into the surrounding interstitium. Understandably, this latter passage may produce serious consequences and therefore passage of blood through this passage should be minimized if not eliminated. To achieve this minimized or zero leakage through this second passage and to further couple the second element and hence the entire prosthesis to the exterior living vessel, the washer 73 is provided. The intent of the washer 73 is to provide a nondegradable matrix for tissue ingrowth replacing the degradable materials as they are resorbed. The washer 73 will be partially degradable and thus, may be fabricated from both degradable and non-degradable materials. Such materials may include poly-L-lactic acid (PLLA) and polyglycolic acid (PGA) as resorbable materials. Polytetrafluoroethylene (PTFE) and Dacron@, manufactured from polyethylene terephtalate, may be used as non-resorbable materials.

The radii of curvature for the flanges of the first and second elements will, by design, be respectively slightly less than and slightly greater than the radius of curvature for a specified vessel lumen with a specific wall thickness. Additionally, the extent of the first and second element geometries will depend on the bifurcation ratio. The amount of intraluminal and extravascular surface area which is in contact with elements 1 and 2 will be dependent on the bifurcation ratio.

Recognizing that blood vessels vary dimensionally within a patient's body, it is anticipated that variously dimensioned apparatus of the instant invention would be required to address anastomoses in various vessels. For this purpose, the invention provides that first and second elements 10 and 20 of different sizes would be color coded to identify specifically dimensioned sizes thereby facilitating ease in selection and use.

It should be appreciated that the embodiments disclosed herein are merely illustrative of the principles of the invention, the scope of the invention being delineated by the claims appended hereto.

What is claimed is:

1. An end to side vascular anastomotic apparatus comprising: a first element defining an interior lumen which extends along the length thereof, said first element including a rigid first tubular portion and a rigid first flange integrally disposed on a first end of said first tubular portion, said first flange defining a convex upper surface; a second element which defines a lumen which extends through the length of said second element and is configured to slidably receive said first tubular portion of said first element; connection structure for interlocking said second element with said first element and for retaining said first tubular element and said first flange in a fixed spatial relationship with a vessel sidewall.

2. The apparatus according to claim 1 wherein said convex upper surface of said first flange is configured to correspond to the internal sidewall of said vessel.

3. The apparatus according to claim 2 wherein said convex upper surface of said first flange is arcuate in configuration.

4. The apparatus according to claim 1 wherein said first tubular portion includes a first longitudinal axis and said first flange includes a second longitudinal axis, and wherein said first element is sufficiently rigid that said first longitudinal axis is spatially fixed relative to said second longitudinal axis.

5. The apparatus according to claim 1 wherein said first tubular portion includes at least one upstanding spline on an exterior surface thereof.

6. The apparatus according to claim 5 wherein said spline is linear in configuration.

7. The apparatus accordingly to claim 1 wherein said first element is coated with a substance adapted to avoid rejection of said apparatus by a patient in which said apparatus is implanted.

8. The apparatus according to claim 4 wherein said first longitudinal axis intersects said second longitudinal axis at an angle between zero degrees and 180 degrees.

9. The apparatus according to claim 8 wherein said first longitudinal axis intersects said second longitudinal axis at an angle between zero degrees and ninety degrees.

10. The apparatus according to claim 1 wherein a second end of said first tubular portion is adapted to receive and retain a vascular graft for facilitating the attachment of said apparatus to a second vessel.

11. The apparatus according to claim 1 wherein said second element includes a second tubular portion and a second flange disposed on a proximal end of said second tubular portion.

12. The apparatus according to claim 11 wherein said second element is rigid.

13. The apparatus according to claim 12 wherein said second tubular portion includes a third longitudinal axis and said second flange includes a fourth longitudinal axis, wherein said third longitudinal axis is spatially fixed relative to said fourth longitudinal axis.

14. The apparatus according to claim 13 wherein said first longitudinal axis is retained spatially fixed relative to said third longitudinal axis upon an engagement of said first element with said second element.

15. The apparatus according to claim 14 wherein said first longitudinal axis is retained spatially fixed in a collinear relationship with said third longitudinal axis upon said engagement of said first element with said second element.

16. The apparatus according to claim 14 wherein said second longitudinal axis is retained spatially fixed parallel with said fourth longitudinal axis upon said engagement of said first element with said second element.

17. The apparatus according to claim 11 wherein said second flange defines a second surface which is concave in configuration.

18. The apparatus according to claim 17 wherein said second surface is configured to correspond to the exterior surface of said blood vessel.

19. The apparatus according to claim 11 wherein said first tubular portion includes at least one spline upstanding from an exterior surface thereof and said second tubular portion defines at least one channel on an interior sidewall surface thereof configured to slidably receive said at least one spline.

20. The apparatus according to claim 19 wherein said spline is linear in configuration.

21. The apparatus according to claim 11 wherein said connection structure comprises at least one tooth like member formed on the exterior surface of said first tubular portion and at least one recess defined within the interior sidewall of said second tubular portion configured to receive and retain said tooth like member.

22. The apparatus according to claim 11 further including a washer is positioned adjacent said second flange.

23. The apparatus according to claim 22 wherein said washer is attached to said second flange.

24. The apparatus according to claim 22 wherein said washer is fabricated from a partially biodegradable material.

* * * * *